(12) United States Patent
Ali et al.

(10) Patent No.: US 11,389,413 B2
(45) Date of Patent: Jul. 19, 2022

(54) METHODS OF PREPARING COMPOSITIONS CONTAINING THYMOQUINONE

(71) Applicant: Jina Pharmaceuticals, Inc., Libertyville, IL (US)

(72) Inventors: Shoukath M. Ali, Vernon Hills, IL (US); Saifuddin Sheikh, Libertyville, IL (US); Ateeq Ahmad, Wadsworth, IL (US); Moghis U. Ahmad, Wadsworth, IL (US); Paul Chen, Libertyville, IL (US); Imran Ahmad, Libertyville, IL (US)

(73) Assignee: Jina Pharmaceuticals, Inc., Libertyville, IL (US)

( * ) Notice: Subject to any disclaimer, the term of this patent is extended or adjusted under 35 U.S.C. 154(b) by 136 days.

(21) Appl. No.: 16/646,891

(22) PCT Filed: Sep. 12, 2018

(86) PCT No.: PCT/US2018/050728
§ 371 (c)(1),
(2) Date: Mar. 12, 2020

(87) PCT Pub. No.: WO2019/055550
PCT Pub. Date: Mar. 21, 2019

(65) Prior Publication Data
US 2021/0008008 A1     Jan. 14, 2021

Related U.S. Application Data

(60) Provisional application No. 62/557,649, filed on Sep. 12, 2017.

(51) Int. Cl.
| | | |
|---|---|---|
| *A61K 9/00* | (2006.01) | |
| *A61K 31/122* | (2006.01) | |
| *A61K 9/06* | (2006.01) | |
| *A61K 9/16* | (2006.01) | |
| *A61K 9/28* | (2006.01) | |
| *A61K 31/355* | (2006.01) | |

(52) U.S. Cl.
CPC .......... *A61K 31/122* (2013.01); *A61K 9/0014* (2013.01); *A61K 9/0053* (2013.01); *A61K 9/06* (2013.01); *A61K 9/1611* (2013.01); *A61K 9/1617* (2013.01); *A61K 9/2853* (2013.01); *A61K 9/2866* (2013.01); *A61K 31/355* (2013.01)

(58) Field of Classification Search
CPC ...... A61K 9/0014; A61K 9/0053; A61K 9/06; A61K 9/1611; A61K 9/1617; A61K 9/2853; A61K 9/2866; A61K 31/122; A61K 31/355
See application file for complete search history.

(56) References Cited

U.S. PATENT DOCUMENTS

| | | | |
|---|---|---|---|
| 2010/0028468 A1 | 2/2010 | Pacioretty et al. | |
| 2013/0022674 A1* | 1/2013 | Dudley | ............. A61P 15/16 |
| | | | 424/456 |
| 2015/0150829 A1 | 6/2015 | Etheve et al. | |
| 2016/0317553 A1* | 11/2016 | Salameh | ............. A61K 9/485 |
| 2017/0210775 A1 | 7/2017 | Ahmad et al. | |

FOREIGN PATENT DOCUMENTS

| | | |
|---|---|---|
| WO | WO 2007/086078 | 8/2007 |
| WO | WO 2015/086239 | 6/2015 |
| WO | WO 2016/005786 | 1/2016 |

OTHER PUBLICATIONS

Ramachandran et al., A novel therapeutic application of solid lipid nanoparticles encapsulated thymoquinone (TQ-SLNs) on 3-nitroproponic acid induced Huntington's disease-like symptoms in wistar rats, Aug. 25, 2016, Chemico-Biological Interactions, vol. 256, pp. 25-36. (Year: 2016).*
International Search Report and Written Opinion for PCT/US2018/050728. dated Dec. 26, 2018. 11 pages.
Extended European Search Report for PCT/US2018/050728. dated Jun. 30, 2021. 8 pages.
Ali et al., Pharmacological and toxicological properties of *Nigella sativa*. Phytother Res. Apr. 2003;17(4):299-305.
Bhatia et al., Tannins in black-plum (*Syzygium cumini* L.) seeds. Biochem J. Jun. 1972;128(1):56P. 1 page.
Bhatti et al., Effect of Prophetic Medicine Kalonji (*Nigella sativa* L.) On Lipid Profile of Human Beings: An In Vivo Approach. 2009, World Applied Sciences J. 6, 1053-1057.
Bourgou et al., Bioactivities of black cumin essential oil and its main terpenes from Tunisia. South African J. Botany, 2010, 76, 210-216.
Burtis et al., Antioxidant activity of *Nigella sativa* essential oil. Phytother Res. Aug. 2000;14(5):323-8.
Chun et al., Biochemical properties of polysaccharides from black pepper. Biol Pharm Bull. Sep. 2002;25(9):1203-8.
Correa et al., Amino acid composition of some *Amaranthus* sp. grain proteins and of its fractions. Arch Latinoam Nutr. Sep. 1986;36(3):466-76.
Dehkordi et al., Antihypertensive effect of *Nigella sativa* seed extract in patients with mild hypertension. Fundam Clin Pharmacol. Aug. 2008;22(4):447-52.
El-Ameen et al., Anti-diabetic Properties of Thymoquinone is unassociated with Glycogen Phosphorylase Inhibition. Pharmacognosy J. 2015, 7, 406-410.

(Continued)

Primary Examiner — Ali Soroush
(74) Attorney, Agent, or Firm — Casimir Jones, S.C.; Mary Ann D. Brow

(57) ABSTRACT

The invention relates to stable preparations of thymoquinone and methods of making and administering stable preparations of thymoquinone. Embodiments of the methods provide compositions comprising thymoquinone with phosphatidylcholine and/or guggulsterol and/or guggulsterol derivatives and/or sodium cholesteryl sulfate, in tablet, capsule, gel, or ointment forms, and method of administering the preparations.

21 Claims, 3 Drawing Sheets

(56) References Cited

OTHER PUBLICATIONS

El-Dakhakhany. Studies on the chemical constituition of Egyptian *Nigella sativa* L. seeds II. The essential oil. Planta Medica, 1963, 11, 465-470.

Entok et al., Anti-inflammatuar and anti-oxidative effects of *Nigella sativa* L.: 18FDG-PET imaging of inflammation. Mol Biol Rep. May 2014;41(5):2827-34.

Ghosheh et al., High performance liquid chromatographic analysis of the pharmacologically active quinones and related compounds in the oil of the black seed (*Nigella sativa* L.) J Pharm Biomed Anal. Apr. 1999;19(5):757-62.

Khader et al., Antimutagenic effects of ethanolic extracts from selected Palestinian medicinal plants. J Ethnopharmacol. Feb. 3, 2010;127(2):319-24.

Mansour et al., Effects of thymoquinone on antioxidant enzyme activities, lipid peroxidation and DT-diaphorase in different tissues of mice: a possible mechanism of action. Cell Biochem Funct. Jun. 2002;20(2):143-51.

Mariod et al., Antioxidant activity and phenolic content of phenolic rich fractions obtained from black cumin (*Nigella sativa*) seedcake. 2009, Food Chem. 116, 306-312.

Salmani et al., Aqueous solubility and degradation kinetics of the phytochemical anticancer thymoquinone; probing the effects of solvents, pH and light. Molecules. May 8, 2014;19(5):5925-39.

Worthen et al., The in vitro anti-tumor activity of some crude and purified components of blackseed, *Nigella sativa* L. Anticancer Res. May-Jun. 1998;18(3A):1527-32.

\* cited by examiner

METHODS OF PREPARING COMPOSITIONS CONTAINING THYMOQUINONE

The present application claims priority to U.S. Provisional Application Ser. No. 62/557,649, filed Sep. 12, 2017, which is incorporated herein by reference.

FIELD OF THE INVENTION

The invention relates to method of making preparations comprising synthetic thymoquinone. The invention further relates to methods of preparing compositions comprising phosphatidylcholine and/or guggulsterol and/or guggulsterol derivatives and/or sodium cholesteryl sulfate. In some embodiments, the invention relates to methods of preparation containing phosphatidylcholine, and guggulsterol or guggulsterol derivatives or sodium cholesteryl sulfate. In certain embodiments, the invention also relates to method of preparing thymoquinone and excipients in a tablet or capsule or topical gel or an ointment. The invention further relates administering preparation to a human subject in the treatment or prevention of diseases. Methods according to the present invention are suitable for practice on an industrial manufacturing scale, and may be practiced, e.g., as a continuous method.

BACKGROUND OF THE INVENTION

Nigella saliva, often referred to as black cumin seed or black caraway seed, is an annual flowering herb that belongs to the family Ranunculaceae, native to south and southwest Asia. *N. sativa* seeds have been used as a spice and a condiment. It has also been used to treat diseases, including asthma, hyperglycemia, urine retention, hypertension, inflammation, cough, and pain (see, e.g., Ali B H, and Bluden, G. 2003; Entok E. et al. 2014; Burtis M. and Bucar, F. 2000; Bourgou S. et al. 2010; Mariod A A et al. 2009).

The biological effects of *N. sativa* are attributed to the various ingredients including thymoquinone, dithymoquinone, thymohydroquinone, and thymol (Omar, A. et al. 1999). *N. sativa* seed contain other ingredients as well, such as carbohydrates, fats, vitamins, proteins, and essential amino acids (Bhatia, I S and Bajaj K. 1972; Chun, H. et al. 2002; Correa, A D et al. 1986). Thymoquinone has also been shown to exert anti-inflammatory, anti-oxidant, and anti-neoplastic effects both in vitro and in vivo (Mansour, M A et al. 2002). Thymoquinone showed activity against human pancreatic adenocarcinoma, uterine sarcoma, and leukemia cell lines, while it is minimally toxic to normal cells (Worthen, D R et al., 1998). Oral administration of thymoquinone in streptozotocin (STZ) and nicotinamide (NA) induced diabetic rats showed antihyperglycemic effects unassociated with glycogen phosphorylase inhibition (El-Ameen, N H M et al., 2015).

Most of the work on thymoquinone has been done at non-clinical level and very few attempts have been made to test its therapeutic effect at the clinical level. An efficacy study of *N. sativa* seed extract was conducted in patients with mild hypertension and the results suggest that the daily use of *N. sativa* seed extract for 2 months may have blood pressure lowering effect in patient with mild hypertension (Dehkordi F R and Kankhah, A. F. 2008). Another report showed that *N. sativa* powder administered to the hypercholesteremia patients for two months was found to reduce the total cholesterol and triglycerides (Bhatti, I U et al. 2009).

Thymoquinone as an active constituent of black cumin seed was first extracted in 1963 (El-Dakhakhany, M. 1963). However, isolation of thymoquinone from *N. sativa* seeds is a cumbersome process and requires large amounts of organic solvents. The essential oil fraction of *N. sativa* constitutes only one percent of the seed oils. Thus, thymoquinone comprises only 0.3 to 0.6% of the fixed oil fractions, which are the most common commercially available product of *N. sativa* (Pacioretty, L M and Babish J G, US 2010/0028468 A1). Considering the low percentage of thymoquinone in the *N. sativa* seed extracts, it is imperative to utilize synthetic thymoquinone to determining its clinical benefits.

Synthetic thymoquinone (2-Isopropyl-5-methyl-1,4-benzoquinone) is a yellow crystalline solid soluble in organic solvents such as ethanol, chloroform, DMSO. It is sparingly soluble in aqueous buffers (approx. 500 µg/mL), which may be enough to exert pharmacological effects if administered via parenteral route. However, thymoquinone is highly unstable in aqueous solutions and is very sensitive to light (Salmani, J M M et al. 2014), limiting its usage in parenteral administration. Hence, there is a need for methods or processes for preparation of stable compositions comprising thymoquinone for oral administration.

SUMMARY OF THE INVENTION

Provided herein are methods of preparing a stable composition containing thymoquinone, preferably synthetic thymoquinone. In some embodiments, the composition comprises phosphatidylcholine and/or one or more of guggulsterol, guggulsterol derivatives, and/or sodium cholesteryl sulfate. In some embodiments, the composition further comprises phosphatidylcholine. In some preferred embodiments, the composition further comprises other excipients. Certain embodiments comprise a method of preparing a stable formulation comprising thymoquinone and administering the preparation to a subject. In certain embodiments, the subject is a mammal. In preferred embodiments, the subject is human.

Provided herein in some embodiments are methods of preparing compositions comprising thymoquinone and guggulsterol for oral delivery to a human subject. In some embodiments, the preparation for oral delivery is in the form of tablet or capsule including gel capsule, pill, dragees, and suppositories. In preferred embodiments, the tablets and/or capsules comprises enteric coating.

Provided herein in some embodiments are methods of preparing a composition comprising thymoquinone and a guggulsterol derivative for oral delivery to a human subject. In some embodiments, oral delivery is in the form of tablet or capsule. In more preferred embodiments, the tablets and/or capsules comprises enteric coating.

Provided herein in some embodiments are methods of preparing a composition comprising thymoquinone and sodium cholesteryl sulfate for oral delivery to a human subject. In some embodiments, the oral delivery is in the form of tablet or capsule. In more preferred embodiments, the tablets and/or capsules comprises enteric coating.

Provided herein in some embodiments are methods of preparing a composition comprising thymoquinone and phosphatidylcholine for oral delivery to a human subject. In some embodiments, the oral delivery is in the form of tablet or capsule. In more preferred embodiments, the tablets and/or capsules comprises enteric coating.

Provided herein in some embodiments are thymoquinone preparations comprising thymoquinone, guggulsterol, and phosphatidylcholine for topical administration to a human subject. In some embodiments, the preparation for topical administration is in the form of a gel, ointment, or cream.

Provided herein in some embodiments are thymoquinone preparations comprising thymoquinone, a guggulsterol derivative, and phosphatidylcholine for topical administration to a human subject. In certain preferred embodiments, the preparation for topical administration is in the form of gel, ointment, or cream.

Provided herein in some embodiments are thymoquinone preparations comprising thymoquinone, sodium cholesteryl sulfate and phosphatidylcholine for topical administration to a human subject. In certain preferred embodiments, the preparation for topical administration is in the form of gel, ointment, or cream.

In some embodiments, a thymoquinone preparation of present invention is co-administered with other drugs. Drugs that can be co-administered along with thymoquinone preparations include but are not limited to anti-diabetic drugs such as metformin, glimepiride, glipizide, glyburide, tolazamide, rosiglitazone, alogliptan, linagliptan, saxagliptin, sitagliptin, insulin, etc.; anticancer drugs such as doxorubicin, paclitaxel, docetaxel, methotrexate, tamoxifen, letrazole, fluvestrant, aromasin, cyclophosphamide, daunomycin, bleomycin, irinotecan, bendamustine, mitoxantrone, ifosfamide, BCNU, streptozotocin, cytrabine, capecitabine, carboplatin, cisplatin, etoposide, 5-flurouracil, etc.; lipid lowering agents such as atorvastatin, simvastatin, rosuvastatin, etc.; anti-inflammatory drugs such as for treating rheumatology, arthritis, psoriasis; antihypertensive agents, such as dihydropyridines, antidepressants, antiallergic agents, etc.; drugs for treating skin diseases such as psoriasis, atopic dermatitis, eczema, melanoma, mycosis, acne, cellulitis, ichthyosis, hives, antifungal agents such as polyene antibiotics or poly antimycotics, azole antifungal drugs, etc. Examples of polyene antibiotic or polyene antimycotics include but not limited to amphotericin B, nystatin, hamycin A & B, aureofungin A & B, natamycin, pimaricin etc. Examples of azole antifungal drugs include but not limited to ketoconazole, itraconazole, fluconazole, etc.

The amount of phosphatidylcholine included in a thymoquinone preparation according to present invention is not limited to any particular amount or percentage (by weight) of the final preparation or weight. In some embodiments, the proportion of phosphatidylcholine is between about 1% to about 90% of the total weight, preferably about 2% to about 80% of the total weight, more preferably about 3% to about 50% of the total weight.

The amount of guggulsterol or guggulsterol derivative or sodium cholesteryl sulfate included in a thymoquinone preparation according to present invention is not limited to any particular amount or percentage (by weight) of the final preparation or weight. In some embodiments, the proportion of guggulsterol or guggulsterol derivative or cholesteryl sulfate is about 0.1% to about 90% of the total weight, preferably about 0.2% to about 50% of the total weight, more preferably about 0.2% to about 25% of the total weight.

The amount of thymoquinone included in a thymoquinone preparation according to present invention is not limited to any particular amount or percentage (by weight) of the final preparation or weight. In some embodiments, the proportion of thymoquinone is about 0.1% to about 90% of the total weight, preferably about 0.5% to about 75% of the total weight, more preferably about 1% to about 50% of the total weight.

In some embodiments, the technology provides a method of preparing a composition comprising thymoquinone comprising:
i) mixing thymoquinone and vitamin E TPGS and melting it together;
ii) preparing lipid granules by sifting lipid and magnesium aluminometasilicate (Neusilin US2) and forming a mixture comprising lipid granules and melted thymoquinone of i) and sifting the resulting mixture, wherein the lipid is selected from the group consisting of phosphatidylcholine, guggulsterol, a guggulsterol derivative, and sodium cholesteryl sulfate;
iii) co-sifting magnesium aluminometasilicate, silicified microcrystalline cellulose (SMCC HD90), cross carmellose sodium, hydrophilic fumed silica; sodium lauryl sulfate, and anhydrous citric acid;
iv) sifting Poloxamer and blending with thymoquinone-lipid granules of ii) and granules of iii); and
v) sifting magnesium stearate and combining with the thymoquinone-lipid granules of iv) and mixing to form a lubricated mixture.

In some embodiments, the lubricated mixture of v) is pressed into tablets, and in certain preferred embodiments, the tablets are seal-coated. In certain embodiments, the seal coating comprises one or more polymers selected from hydroxymethyl propyl cellulose, methyl hydroxyethylcellulose, ethyl cellulose, hydroxypropylcellulose, hydroxypropyl methylcellulose, povidone, sodium carboxy methylcellulose, acrylate polymer, Opadri, and polyethylene glycol. In some embodiments, the seal-coated tablets are enteric coated with polymers, and in some embodiments, the enteric coating comprises one or more polymers selected from hydroxypropyl methyl cellulose phthalate, cellulose acetate phthalate, acrylate polymers, and polyvinyl acetate phthalate, Opadri enteric, Eudragit, and Acryl-EZE.

In certain embodiments of any embodiments of the tablets described above, the amount of thymoquinone in a single tablet is at least 50 mg, preferably at least 500 mg, more preferably at least 1000 mg. In certain embodiments of any embodiments of the tablets described above, the guggulsterol or guggulsterol derivative in a single tablet is between 10 mg and 1000 mg, preferably between 25 mg and 50 mg. In certain embodiments of any embodiments of the tablets described above, the phosphatidylcholine in a single tablet is between 10 mg and 500 mg, preferably between 10 and 250 mg, more preferably between 10 and 100 mg In some embodiments, the technology provides a method of preparing a gel or ointment composition comprising thymoquinone, phosphatidylcholine, guggulsterol or guggulsterol derivative or sodium cholesteryl sulfate, comprising:
i) mixing phosphatidylcholine, guggulsterol, or guggulsterol derivative or sodium cholesteryl sulfate and thymoquinone in a first organic solvent;
ii) diluting the mixture of i) with a second organic solvent; and
iii) mixing the diluted mixture of ii) with a gelling agent to form a uniform viscous gel or ointment.

In some embodiments, the phosphatidylcholine used in the method described above is selected from phosphatidylcholine includes soy phosphatidylcholine, hydrogenated soy phosphatidylcholine, dimyristoylphosphatidylcholine, distearoylphosphatidylcholine, dipalmitoylphosphatidylcholine, dioleoylphosphatidycholine, egg phosphatidylcholine.

In any of the embodiments described above, the guggulsterol derivative guggulsteryl sulfate, guggulsteryl phosphate, guggulsteryl phosphocholine, guggulsteryl phosphoglycerol, fatty acid esters of guggulsterol, and polyethylene glycol (PEG) derivatives of guggulsterol. In certain embodiments, the fatty acid esters of guggulsterol include guggulsterol include guggulsteryl acetate, guggulsteryl propionate, guggulsteryl butyrate, guggulsteryl valerate, guggulsteryl hexanoate, guggulsteryl caprylate, guggulsteryl caprates, guggulsteryl laurate, guggulsteryl myrstate, guggulsteryl palmitate, guggulsteryl stearate, guggulsteryl oleate, guggulsteryl linoleate, guggulsteryl linolenate, guggulsteryl eicosapentenoate, guggulsteryl arachidonate, guggulsteryl hemisuccinate, guggulsteryl succinate. In certain embodiments, the molecular weight of PEG in PEG derivatives of guggulsterol is between 500 and 2000.

In certain embodiments of any of the embodiments described above, the guggulsterol or guggulsterol derivative may be in the form of Z-isomer, and/or may be in the form of sodium salt.

In some embodiments of the method of preparing a gel or ointment composition, aid gelling agent is selected from hydroxypropylmethylcellulose, sodium carboxymethylcellulose, methyl cellulose, Simulgel INS 100, carbomers, Guar gum, and gelatin.

In any of the embodiments of the method of preparing a gel or ointment composition described above, the first organic solvent and second organic solvent may be the same or different. In certain embodiments, the first organic solvent and second organic solvent is selected from isopropyl alcohol, ethanol, propylene glycol, polyethylene glycols, oleic acid, oleoyl alcohol, mineral oil, and purified water.

In any of the embodiments of the method of preparing a gel or ointment composition described above, the amount of thymoquinone in the gel or ointment may be between 0.1% and 10% by weight, preferably 3% by weight; the quantity of the phosphatidylcholine in the gel or ointment may be between 1% and 20% by weight, preferably 6% by weight; and/or the amount of guggulsterol or guggulsterol derivative in a gel or ointment may be between 0.1% and 10% by weight, preferably 0.5% by weight.

In some embodiments, the technology provides a method of administering thymoquinone to a subject, comprising:
 i) providing a composition comprising thymoquinone prepared according to any of the embodiments described above; and
 ii) administering the preparation to a subject.

In some embodiments, the composition is a tablet or capsule and the administering comprises oral administration; while in some embodiments, the composition comprises a gel or ointment and the administering comprises topical administration. In preferred embodiments, the subject is a human.

Definitions

To facilitate an understanding of the present invention, a number of terms and phrases are defined below:

As used herein, the term "composition" "preparation" or "formulation" refers to the combination of an active agent (e.g. an active pharmaceutical compound) with a carrier, inert or active, excipients, making the composition especially suitable for diagnostic or therapeutic use in vitro, in vivo, or ex vivo.

As used herein, the terms "synthetic thymoquinone" or "thymoquinone" refers to thymoquinone that was synthesized (i.e., was not isolated from extract of a plant), e.g., in a laboratory starting from commercially available starting materials. The synthesis of said thymoquinone may be by any route of synthesis and involves any number of synthetic steps.

As used herein, the term "active" as used in reference to an agent, composition, or compound, refers to an agent that, upon administration or application, causes a beneficial, desired, or expected result. The administration may be in one or more administrations, applications, dosages and is not intended to be limited to a particular formulation or administration route. The term is not limited to any particular level of activity. For example, a formulation of an active agent need not have the same level of activity as a different formulation of an active agent, so long as the active agent in the formulation is sufficiently active that an effective amount of the active agent can be administered by administration of the formulation of the agent.

The terms "agent" and "compound" are used herein interchangeably to refer to any atom, molecule mixture or more complex composition having an attributed feature. For example, an 'active agent" or "active compound" refers to any atom, molecule, preparation mixture, etc. that, upon administration or application, causes beneficial, desired or expected result.

As used herein, the term "administration" or "administering" refers to the act of giving a drug, or active agent, or therapeutic treatment (e.g. composition of the present invention) to a physiological system (e.g., a subject or in vivo, in vitro, or ex vivo cells, tissues, and organs). Exemplary routes of administration to the human body can be through mouth (oral), skin (transdermal), eyes (ophthalmic), nose (nasal), injection (parenteral) and the like. Administration may be in one or more administrations, applications, or dosages, and is not intended to be limited to a particular administration route.

As used herein, the term "co-administration" refers to the administration of at least two agents(s) (e.g. two separate compositions, containing different active agents) or therapies to a subject. In some embodiments, the co-administration of two or more agents or therapies are concurrent. In other embodiments, a first agent/therapy is administered prior to a second agent/therapy. Those of skill in the art understand that the formulations and/or routes of administration of the various agents or therapies used may vary. The appropriate dosage for co-administration can be readily determined by one skilled in the art.

As used herein, the term "excipient" refers to an inactive ingredient (i.e. not pharmaceutically active) added to the preparation of active ingredient The disintegrates, antiadherants, binders, plasticizers, fillers, coatings, lubricants, preservatives, glidants, enhancers, wetting agents, emulsifying agent, solubilizing agent, dispersing agent, flavors, colors, sorbents, sweetener, antioxidants, permeation enhancer, humectant, emulsifying agent, ointment base, acidifying and/or alkalizing and/or buffering agent, gelling and protective agents described herein may be referred to generally as "excipients".

As used herein, the term "disease" refers to a state, signs, and/or symptoms that are associated with any impairment of the normal state of a living animal or any of its organs or tissues that interrupts or modifies the performance of normal functions and may be a response to environmental factors.

As used herein, the term "treatment" or grammatical equivalents encompasses the improvement and/or reversal of the symptoms of disease (e.g. diabetes), or reduction of risk of occurrence of disease. A compound which causes an improvement in any parameter associated with disease when used in the screening methods of the instant invention may thereby be identified as a therapeutic compound. The term "treatment" refers to both therapeutic treatment and prophylactic or preventive measures. For example, those who may benefit from treatment with compositions and methods of the present invention include those already with a disease and/or disorder (e.g. diabetes, or symptoms or pathologies consistent with diabetes) as well as those in which a disease and/or disorder is to be prevented (e.g., using a prophylactic treatment of the present invention).

As used herein, the term "oral" refers to application of the compositions of the present invention through mouth. The term oral also includes application of composition through buccal sublabial, sublingual administration.

As used herein, the term "topically" refers to application of the compositions of the present invention to the surface of the skin and mucosal cells and tissues (e.g., alveolar, buccal, lingual, masticatory, or nasal mucosa, and other tissues and cells which line hollow organs or body cavities).

As used herein, the term "transdermal" refers to application of the compositions of the present invention in a form for absorption through the skin into the bloodstream. For example, composition of present invention can be applied in the form of patch (e.g. transdermal patch) to deliver the active agent at a constant rate for a specific period of time, allowing the bioavailability and effectiveness of the drug to remain constant.

The term "polyethylene glycol (PEG) includes polymers of lower alkylene oxide, in particular ethylene oxide (polyethylene glycols) having an esterifiable hydroxyl group at least one end of the polymer molecule, as well as derivatives of such polymers having esterifiable carboxy groups. Polyethylene glycols of an average molecular weight ranging from 200-20,000 are preferred; those having an average molecular weight ranging from 300-2000 are particularly preferred.

The use of terms "a" and "an" and "the" and similar referents in the context of describing the invention (especially in the context of the following claims) are to be construed to cover both the singular and the plural, unless otherwise indicated herein or clearly contradicted by context. The terms "comprising", "including", "having", and "containing" are to be construed as open-ended terms (i.e. meaning "including but not limited to") unless otherwise noted. The use of any and all examples, or exemplary language (e.g. 'such as") provided herein, is intended merely to better illuminate the invention and does not pose a limitation on the scope of the invention unless otherwise claimed. No language in the specifications should be constructed as indicating any non-claimed element as essential to the practice of the invention.

DETAILED DESCRIPTION OF THE INVENTION

Figure 1:
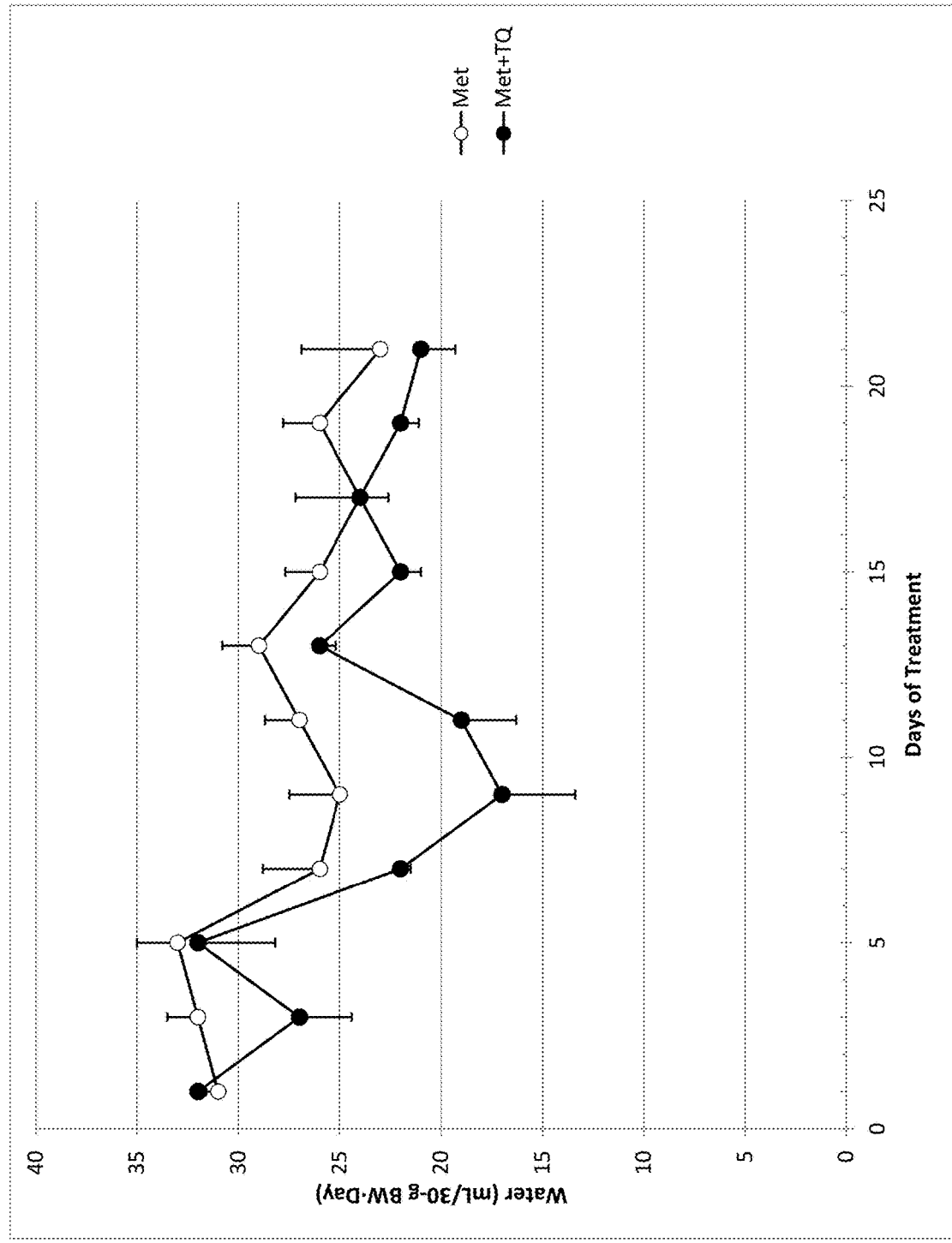
FIG. 1 shows a graph comparing water consumption in a Metformin (Met)-treated group and in a Thymoquinone/Metformin (TQ/Met)-treated group, as described in Example 22.

The invention relates to a method of preparing a thymoquinone or synthetic thymoquinone formulation. In some embodiment, the invention comprises administrating a thymoquinone preparation to a human subject, e.g., to treat a disease. In certain embodiments, the preparation comprising thymoquinone or synthetic thymoquinone comprises phosphatidylcholine and/or guggulsterol or a guggulsterol derivative or sodium cholesteryl sulfate. In other embodiments, the preparation comprises phosphatidylcholine and/or guggulsterol, a guggulsterol derivative, or sodium cholesteryl sulfate.

Particular embodiments of the invention are described in the Summary, and in this Detailed Description of the Invention. Although the invention has been described in connection with specific embodiments, it should be understood that the invention as claimed should not be unduly limited to such specific embodiments.

Examples of guggulsterol derivatives suitable for use in the methods and preparation of the present invention include guggulsteryl sulfate, guggulsteryl phosphate, guggulsteryl phosphocholine, guggulsteryl phosphoglycerol, fatty acid esters of guggulsterol, and polyethylene glycol (PEG) derivatives of guggulsterol. Examples of fatty acid esters of guggulsterol include but not limited to guggulsteryl acetate, guggulsteryl propionate, guggulsteryl butyrate, guggulsteryl valerate, guggulsteryl hexanoate, guggulsteryl caprylate, guggulsteryl caprates, guggulsteryl laurate, guggulsteryl myrstate, guggulsteryl palmitate, guggulsteryl stearate, guggulsteryl oleate, guggulsteryl linoleate, guggulsteryl linolenate, guggulsteryl eicosapentenoate, guggulsteryl arachidonate, guggulsteryl hemisuccinate, guggulsteryl succinate. Examples PEG derivatives of guggulsterol include but not limited to the average molecular weight of PEG ranging from 200-20,000, while in certain preferred embodiments, the average molecular weight of the PEG in a PEG derivative of guggulsterol is in between 500-2000.

The present invention provides methods of making preparations comprising synthetic thymoquinone and methods of delivering such preparations to a subject, e.g., a human subject. Any suitable amount of synthetic thymoquinone sufficient to produce a desired effect, e.g., a therapeutic effect, can be used. In preferred embodiments, suitable amounts of thymoquinone are those amounts that can be suitably incorporated into a tablet, capsule including gel capsule, pill, dragees, suppositories, gel, ointment, cream of the present invention. When desired, the tablets or capsules can be enteric-coated to protect it from acids in the stomach.

Synthetic thymoquinone in the present invention is either obtained commercially or synthesized in the laboratory by any known method of synthesis. In preferred embodiments, amount of thymoquinone in a tablet or capsule containing thymoquinone and excipients is in between 10 mg and 5000 mg such as in between 10 mg and 4000 mg or 10 mg and 10 mg and 3000 mg. In preferred embodiments, the quantity of thymoquinone in a tablet or capsule containing thymoquinone and excipients is in between 10 mg and 2000 mg.

In some embodiments, the amount of guggulsterol or guggulsterol derivative or sodium cholesteryl sulfate in a tablet or capsule containing thymoquinone, guggulsterol or guggulsterol derivative or sodium cholesteryl sulfate and excipients is in between 10 mg and 5000 mg such as in between 10 mg and 4000 mg or 10 mg, 10 mg and 3000 mg and 10 mg and 2000 mg. In preferred embodiments, the quantity of thymoquinone in a tablet or capsule containing thymoquinone and excipients is in between 10 mg and 2000 mg.

In some embodiments, the amount of phosphatidylcholine in a tablet or capsule containing thymoquinone, phosphatidylcholine and excipients is in between 10 mg and 1000 mg such as in between 10 mg and 750 mg or 10 mg and 500 mg and 10 mg and 250 mg. In preferred embodiments, the quantity of thymoquinone in a tablet or capsule containing thymoquinone and excipients is in between 10 mg and 2000 mg Guggulsterol or guggulsterol derivative in the present invention is in the form of Z-isomer or E-isomer or mixture of Z- and E-isomer. In more preferred embodiments, guggulsterol or guggulsterol derivative is in the form Z-isomer. In some embodiments, guggulsteryl sulfate is in the form of salt. Examples of salts of guggulsteryl sulfate include but not limited to sodium, potassium, ammonium, calcium salts. In most preferred embodiments, the salt sodium salt.

In some embodiments, a thymoquinone preparation contains disintegrants. Disintegrants expand and dissolve when wet, causing the tablets to break apart in the digestive tract, releasing the active ingredients for absorption. Examples of disintegrants that find use in the present invention include but are not limited to crosslinked polymers such as crosslinked sodium carboxymethylcellulose (also known as cross carmellose or croscarmellose), crosslinked polyvinylpyrrolidone (also known as cross povidone or crospovidone); starches, clays, cellulose, magnesium aluminometasilicate (Neusilin US2), modified starches such as Primogel®, Explotab®, and sodium starch glycolate.

In some embodiments, a thymoquinone preparation contains binders. A binder holds the ingredients in a tablet together and improves free flow qualities by formulation of granules to desired hardness and size. Examples of binders that find use in the present invention include but are not limited to cellulose, microcrystalline cellulose, methyl cellulose, hydroxypropylcellulose, carboxymethylcellulose, polyvinylpyrrolidone, aluminometasilicate (Neusilin US2), glucose, sucrose, lactose, povidone, starch, gelatin, sugar alcohols such as xylitol, sorbitol, maltitol.

In some embodiments, a thymoquinone preparation contains permeation or absorption enhancers. Enhancer increases the permeation or absorption by promoting diffusion, partitioning, or the drug solubility of an active ingredient. Example of permeation or absorption enhancers that find use in the present invention include but are not limited to Vitamin E-PEG1000 succinate (TPGS), silicified microcrystalline cellulose (SMCC HD90), Poloxamers, stearic acid, oleic acid, magnesium stearate, calcium stearate, surfactants, propylene glycol, polyethylene glycol, vegetable oil.

In some embodiments, a thymoquinone preparation contains emulsifying or solubilizing agent. Example of emulsifying or solubilizing agent that find use in the present invention include but are not limited to Poloxamer, sorbitan monostearate, sorbitan monooleate, sodium lauryl sulfate, propylene glycol monostearate, polysorbate 20, polysorbate 60, polysorbate 80, docusate sodium.

In some embodiments, a thymoquinone preparation contains lubricants. Lubricants prevent ingredients from clumping together and from sticking to the tablet punches or capsule filling machine. Example of lubricants that find use in the present invention include but are not limited to stearic acid, magnesium stearate, calcium stearate, surfactants, polyethylene glycol, vegetable oil.

In some embodiments, a thymoquinone preparation contains glidant. Glidants are used commonly to improve the flow characteristics of a powder mixture by reducing friction between particles. Examples of glidants that find use in the present invention include but are not limited to colloidal silicone dioxide such as Carbosil®, Aerosil®, fumed silica, talc, corn starch, and magnesium carbonate.

In some embodiments, a thymoquinone preparation contains diluents or fillers. Diluents or fillers normally make up the bulk of solid unit dosage forms when drug itself is inadequate to produce the bulk. Examples of diluents or fillers that find use in the present invention include but are not limited to dextrose, lactose, starches, sorbitol, mannitol, microcrystalline cellulose, aluminometasilicate (Neusilin US2), dibasic calcium phosphate, calcium carbonate, and magnesium stearate.

In some embodiments, a thymoquinone preparation contains plasticizers. Plasticizers are added to produce elasticity and flexibility to the coating materials in case of tablets, determine hardness of capsule shell in case of soft gelatin capsule and impart softness and resilience to suppositories. Examples of plasticizers that find use in the present invention include but are not limited to diacetylated monoglycerides, castor oil, polyethylene glycol, polypropylene glycol, triethyl citrate, and triacetin.

In some embodiments, a thymoquinone preparation contains wetting agent. Wetting agent is added to help in the dispersion or dissolution of hydrophobic active ingredient. Examples of wetting agent that find use in the present invention include but are not limited to sodium lauryl sulfate (SLS), polysorbate 20, polysorbate 60, polysorbate 80, lecithin.

In some embodiments, a thymoquinone preparation contains coating material. The coatings of tablets or capsules protect ingredients from deterioration from moisture present in the air. Examples of coating materials that find use in the present invention include but are not limited to hydroxypropylmethyl cellulose (HMPC), synthetic polymers, polysaccharides, povidone, ethyl cellulose, gelatin, shellac, and Opadri®.

In some embodiments, a thymoquinone preparation further contains enteric coating materials. Enteric coatings control that rate of drug release and determine where the drug will be released in the digestive tract. Examples of enteric coating materials that find use in the present invention include but not limited to hydroxypropyl methylcellulose phthalate (HPMCP), cellulose acetate phthalate (CAP), poly (methacrylic acid-co-methyl methacrylate, cellulose acetate trimellitate (CAT), polyvinyl acetate phthalate (PVAP), esters of aleurtic acid (shellac), Opadri® enteric, Eudragit®, and Acryl-EZE®.

In some embodiments, a thymoquinone preparation contains acidifying or alkalizing or buffering agent. Examples of acidifying or alkalizing or buffering agent that find use in the present invention include but not limited to citric acid, phosphoric acid, acetic acid, sodium hydroxide, hydrochloric acid, monosodium phosphate, triethanolamine.

In some embodiments, a thymoquinone preparation contains coloring agents. Colors are added to improve the appearance and identification of a product. Examples of coloring agents that find use in the present invention include but not limited to FD and C, D, and C dyes and lakes.

In some embodiments, a thymoquinone preparation contains sweeteners. Sweeteners are added to impart sweet taste to the formulation especially in chewable tablets. Examples of sweeteners that find use in the present invention include but not limited to mannitol, saccharin, etc.

In some embodiments, the compositions of the present invention further contain flavors. Flavors are added, e.g., to mask the unpleasant taste of the active ingredients. Examples of flavors that find use in the present invention include but not limited to natural or artificial flavors. Examples of natural flavors are fruit extracts such as cherry, mint, peach, apricot raspberry, orange, vanilla extract, etc.

Pharmaceutical preparations that find use with the method of the present invention include but not limited to tablets, capsules, pills, dragees, suppositories, solutions, suspensions, ointments, and gels. For the oral mode of administration, preferred forms of formulation include tablets, capsules, lozenges, and powders. For topical application and suppositories, preferred forms of formulation comprise gels, ointments, creams, and the like.

When desired, a preparation containing thymoquinone or thymoquinone, phosphatidylcholine and or guggulsterol, or a guggulsterol derivative or sodium cholesteryl sulfate formulation can be encapsulated in enteric-coated tablets or enteric coated-capsules to protect it from acids in the stomach. The term "enteric" refers to a small intestine, and enteric coatings prevent release of medication before it reaches the small intestine. Most enteric coatings work by presenting a surface that is stable at acidic pH but breaks down rapidly at higher pH.

In some embodiments, thymoquinone, guggulsterol, a guggulsterol derivative or sodium cholesteryl sulfate are mixed with one or more excipients such as cross carmellose sodium, polyvinylpyrrolidone, microcrystalline cellulose, and aerosol and passed through sieve to form granules. In some embodiments, the granules may further contain phosphatidylcholine. In some embodiments these granules are mixed with lubricants such as steric acid and compressed into tablets. In preferred embodiments, the tablets are seal coated, e.g., with polymers such as hydroxypropyl methylcellulose. In particularly preferred embodiments, the seal coated tablets are further enteric coated with polymers such as Acryl-EZE®, or Opadry® enteric.

In some embodiments, thymoquinone, guggulsterol, a guggulsterol derivative or sodium cholesteryl sulfate are mixed with one or more excipients such as microcrystalline cellulose, and aerosol and passed through sieve to form granules. In some embodiments, the granules further contain phosphatidylcholine. In some embodiments, these granules are mixed with microcrystalline cellulose, croscarmellose sodium, lactose, and poloxamer 188 and compressed into tablets. In preferred embodiments, the tablets are seal coated with polymers such as hydroxypropyl methylcellulose or Opadry® clear. In particularly preferred embodiments, the seal coated tablets are further enteric coated with polymers such as Acryl-EZE®, Eudragit®, and Opadry® enteric.

In some embodiments, a method of present invention comprises preparation of a gel comprising thymoquinone, phosphatidylcholine, guggulsterol and other excipients. In other embodiments, the method comprises preparation of gel comprising thymoquinone, phosphatidylcholine, a guggulsterol derivative and other excipients. In yet other embodiments, the method of present invention comprises preparation of gel comprising thymoquinone, phosphatidylcholine, sodium cholesteryl sulfate and other excipients.

In some embodiments, compositions of the present invention contain phosphatidylcholines. Examples of phosphatidylcholines that find use in the present invention include but not limited to soy phosphatidylcholine, hydrogenated soy phosphatidylcholine, dimyristoylphosphatidylcholine, distearoylphosphatidylcholine, dipalmitoylphosphatidylcholine, dioleoylphosphatidycholine, egg phosphatidylcholine, and mixtures thereof.

In some embodiments, the present invention includes fatty acids or salts of fatty acids. In some preferred embodiments, fatty acids that find use in the present invention include but are not limited to oleic acid, stearic acid, caproic acid, palmitic acid, eicosanoic acid, palmitoleic acid, linolenic acid, and mixtures thereof. Different salts of fatty acids include but not limited to sodium salt, magnesium salt, calcium salt, potassium salt, etc.

In some embodiments, compositions of the present invention contain one or more gelling agents. Example of gelling agents that find use in the present invention include but are not limited to carbomer polymers, such as Carbopol® 934, carboxymethyl cellulose, hydroxypropyl cellulose, hydroxypropyl methylcellulose, sodium carboxymethyl cellulose, pemulen, hydroxyethyl acrylate/sodium acryloyl dimethyltaurate copolymer and isohexadecane and polysorbate 60 (Simulgel® INS 100); alginate, poloxamer, xanthum gum, etc.

In some embodiments, compositions of the present invention contain emollients. Emollients assist in the penetration of active ingredient through skin. Example of emollients that find use in the present invention include but are not limited to isopropyl myristate, isopropyl palmitate isopropyl stearate, glycerin, mineral oil, coconut oil, olive oil, sesame oil, mustard oil, almond oil, petrolatum, etc.

In some embodiments, compositions of the present invention contain preservatives. Examples of preservatives include but not limited to methyl paraben, propyl paraben, benzyl alcohol, sodium benzoate, imidazolidinyl urea, etc.

In some embodiments, compositions of the present invention include alcohols or mixture of alcohols. Examples of alcohols that find use in the present invention includes but are not limited to ethanol, isopropyl alcohol, butyl alcohol, propylene glycol, cetyl alcohol, ethylene glycol, hexylene glycol, oleoyl alcohol, etc.

In some embodiments, the present invention further comprises polyethylene glycols (PEG). In some embodiments, the PEG has an average molecular weight ranging from 200-20,000, while in certain preferred embodiments the average molecular weight of the PEG is in between 300-2000.

In some embodiments, compositions of the present invention include antioxidants. Examples of antioxidants include but are not limited to alpha tocopherol, ascorbic acid, butyl hydroxyl toluene, butyl hydroxyl anisole, etc.

In some embodiments, compositions of the present invention contain thymoquinone about 0.1% to about 90% of the total weight, preferably about 0.5% to about 75% of the total weight, more preferably about 1% to about 50% of the total weight.

In some embodiments, the amount of thymoquinone in a single tablet or capsule is between 25 mg and 2000 mg, preferably between 25 mg and 1000 mg and more preferable between 50 mg and 500 mg.

In some embodiments, a preparation of the present invention contains phosphatidylcholine about 1% to about 90% of the total weight, preferably about 2% to about 80% of the total weight, more preferably about 3% to about 50% of the total weight.

In some embodiments, a preparation of the present invention comprises guggulsterol about 0.1% to about 90% of the total weight, preferably about 0.2% to about 75% of the total weight, more preferably about 0.2% to about 50% of the total weight.

In some embodiments, a preparation of the present invention comprises a guggulsterol derivative about 0.1% to about 90% of the total weight, preferably about 0.2% to about 75% of the total weight, more preferably about 0.2% to about 50% of the total weight.

In some embodiments, a preparation of the present invention comprises sodium cholesteryl sulfate about 0.1% to about 90% of the total weight, preferably about 0.2% to about 75% of the total weight, more preferably about 0.2% to about 50% of the total weight.

In some embodiments, a method of preparing a composition of the invention comprises dissolving thymoquinone (e.g., synthetic thymoquinone), guggulsterol or a guggulsterol derivative or sodium cholesteryl sulfate and phosphatidylcholine in first organic solvent until it forms a clear solution. Subsequently, a second organic solvent and an emulsifying polymer (e.g., Simulgel® INS 100) are added while stirring to form a uniform viscous gel. The first organic solvent and the second organic solvent may be the same or different, and are preferably selected from ethanol, isopropyl alcohol, propylene glycol, PEG400, butyl alcohol, cetyl alcohol, ethylene glycol, hexylene glycol, oleoyl alcohol. In more preferred embodiments, the first organic solvent is isopropyl alcohol, and the second organic solvent is propylene glycol.

In some embodiments, the method of preparation comprises dissolving thymoquinone, phosphatidylcholine in first organic solvent until it forms a clear solution. Subsequently, second organic solvent and Carbopol® polymer is added under stirring to form a uniform viscous gel. In some embodiments, the first organic solvent and the second organic solvent are the same or different, and are selected from ethanol, isopropyl alcohol, propylene glycol, PEG400, butyl alcohol, cetyl alcohol, ethylene glycol, hexylene glycol, oleoyl alcohol. In more preferred embodiments, the first organic solvent is isopropyl alcohol, and the second organic solvent is propylene glycol. In some embodiments, alpha-tocopherol is also added in the first organic solvent.

In some embodiments, thymoquinone, guggulsterol or a guggulsterol derivative or sodium cholesteryl sulfate and soy phosphatidylcholine are dissolved in isopropyl alcohol. Carbopol® polymer, alpha-tocopherol, and propylene glycol are added under stirring to form a uniform viscous gel.

In some embodiments, thymoquinone is mixed in polysorbate 80 and propylene glycol and the mixture is diluted with 0.9% sodium chloride and sonicated or stirred to form a clear solution.

In some embodiments, thymoquinone is mixed in polysorbate 80 and ethanol and the mixture is diluted with 0.9% sodium chloride and sonicated or stirred to form a clear solution In some embodiments, thymoquinone is dissolved in ethanol. Thymoquinone and corn oil are added and stirred or sonicated until a clear solution is obtained.

The preparation of the present invention may be administered in any dosage form and via any system that delivers the active compound thymoquinone in vivo. In some embodiments, a composition of present invention is delivered by "percutaneous administration", e.g. delivering the drug from the surface of patient's skin, through the stratum corneum, epidermis, and dermis layers, and into the microcirculations. This is generally accomplished by diffusion down a concentration gradient. The diffusion may occur via intracellular penetration (through the cells), intercellular penetration (between the cells), transappendageal penetration (through the hair follicles, sweat, and sebaceous glands), or any combination of the above.

For topical administration, a preparation of the invention containing thymoquinone may be delivered in the form of ointment, gel, emulsion, cream. In some embodiments, the formulation comprises excipient additives including but not limited to oils such as vegetable oil, mineral oil, olive oil, sesame oil, castor oil, corn oil, vitamin E oil, and the like; hydrocarbons such as paraffin's, petroleum jelly, glycerin glycol, polyethylene glycols, polymers, etc.

In some embodiments, a preparation of the invention containing thymoquinone may be delivered as transdermal patch. The patch may comprise (i) a solution-impermeable backing foil, (ii) a layer like element having a cavity, (iii) a microporous or semipermeable membrane, (iv) a self-adhesive layer, and (v) optionally a removable backing film. The layer-like element having a cavity may be formed by the backing foil and the membrane. Alternatively, the patch may comprise (i) a solution-impermeable backing foil, (ii) an open-pored foam, a tissue like layer or a fibrous web-like layer as reservoir, (iii) a self-adhesive layer, and (iv) optionally a removable backing film.

EXPERIMENTAL EXAMPLES

Example 1

Z-Guggulsterol (50 mg) was dissolved in 1 mL of ethanol and Thymoquinone (400 mg) was added followed by the addition of corn oil (9 mL). The suspension was stirred or sonicated until a clear solution was obtained.

Example 2

Z-Guggulsterol (90 mg) was dissolved in 0.3 mL of ethanol. Thymoquinone (400 mg) was added followed by corn oil (2.7 mL), as described in Example 1. The suspension was stirred or sonicated until a clear solution was obtained.

Example 3

Z-Guggulsteryl sulfate (90 mg) was dissolved in 0.3 mL of ethanol. Thymoquinone (400 mg) was added followed by corn oil (2.7 mL), as described in Example 1. The suspension was stirred or sonicated until a clear solution was obtained.

Example 4

Sodium Cholesteryl sulfate (90 mg) was dissolved in 0.3 mL of ethanol. Thymoquinone (400 mg) was added followed by corn oil (2.7 mL), as described in Example 1. The suspension was stirred or sonicated until a clear solution was obtained.

Example 5

Z-Guggulsterol (10 mg) was dissolved in 0.1 mL of ethanol. Thymoquinone (80 mg) was added, followed by polysorbate 80 (0.4 mL). The suspension was stirred or sonicated until a clear solution was obtained.

Example 6

Z-Guggulsteryl sulfate (10 mg) was dissolved in 0.1 mL of ethanol. Thymoquinone (80 mg) was added, followed by polysorbate 80 (0.4 mL). The suspension was stirred or sonicated until a clear solution was obtained.

Example 7

Sodium Cholesteryl sulfate (10 mg) was dissolved in 0.1 mL of ethanol. Thymoquinone (80 mg) was added, followed by polysorbate 80 (0.4 mL). The suspension was stirred or sonicated until a clear solution was obtained.

Example 8

Thymoquinone (120 mg) is mixed in propylene glycol (23.68 g) and polysorbate 80 (2.64 g). 0.9% sodium chloride solution (23.68 g) was added and stirred or sonicated until a clear solution was obtained.

Example 9

Z-Guggulsterol (50 mg) and soy phosphatidylcholine (600 mg) were mixed in isopropyl alcohol (3 g) and stirred until a clear solution was formed. Thymoquinone (300 mg) was added and stirring was continued until it dissolved completely. Propylene glycol (5.65 g) and Simulgel INS 100 (400 mg) were added under stirring to form a uniform viscous gel.

Example 10

Z-Guggulsteryl sulfate (50 mg) and soy phosphatidylcholine (600 mg) were mixed in isopropyl alcohol (3 g) and stirred until a clear solution was formed. Thymoquinone (300 mg) was added and stirring was continued until it dissolved completely. Propylene glycol (5.65 g) and Simulgel INS 100 (400 mg) were added under stirring to form a uniform viscous gel.

Example 11

Sodium cholesteryl sulfate (50 mg) and soy phosphatidylcholine (600 mg) were taken in isopropyl alcohol (3 g) and stirred until a clear solution was formed. Thymoquinone (300 mg) was added and stirring was continued until it dissolved completely. Propylene glycol (5.65 g) and Simulgel INS 100 (400 mg) were added under stirring to form a uniform viscous gel.

Example 12

Z-Guggulsterol (65 mg) and soy phosphatidylcholine (600 mg) were combined with isopropyl alcohol (4.8 g) and stirred until a clear solution was formed. Thymoquinone (300 mg) was added and stirring was continued until it dissolved completely. Propylene glycol (3.98 g) and Carbopol polymer (250 mg) and alpha tocopherol (5 mg) were added under stirring to form a uniform viscous gel.

Example 13

Z-Guggulsteryl sulfate (65 mg) and soy phosphatidylcholine (600 mg) were combined with isopropyl alcohol (4.8 g) and stirred until a clear solution was formed. Thymoquinone (300 mg) was added and stirring was continued until it dissolved completely. Propylene glycol (3.98 g) and Carbopol polymer (250 mg) and alpha tocopherol (5 mg) were added under stirring to form a uniform viscous gel.

Example 14

Sodium Cholesteryl sulfate (65 mg) and soy phosphatidylcholine (600 mg) were mixed in isopropyl alcohol (4.8 g) and stirred until a clear solution was formed. Thymoquinone (300 mg) was added and stirring was continued until it dissolved completely. Propylene glycol (3.98 g) and Carbopol polymer (250 mg) and alpha tocopherol (5 mg) were added under stirring to form a uniform viscous gel.

Example 15

Z-Guggulsteryl sulfate (65 mg) and soy phosphatidylcholine (600 mg) were mixed in isopropyl alcohol (4.8 g) and stirred until a clear solution was formed. Thymoquinone (300 mg) was added and stirring was continued until it dissolved completely. Propylene glycol (3.98 g) and Carbopol polymer (250 mg) and alpha tocopherol (5 mg) were added under stirring to form a uniform viscous gel.

Example 16

Sodium Cholesteryl sulfate (65 mg) and soy phosphatidylcholine (600 mg) were combined in isopropyl alcohol (4.8 g) and stirred until a clear solution was formed. Thymoquinone (300 mg) was added and stirring was continued until it dissolved completely. Propylene glycol (3.98 g) and Carbopol polymer (250 mg) and alpha tocopherol (5 mg) were added under stirring to form a uniform viscous gel.

Example 17

Soy phosphatidylcholine (600 mg) was taken in isopropyl alcohol (4.8 g) and stirred until a clear solution was formed. Thymoquinone (300 mg) was added and stirring was continued until it dissolved completely. Propylene glycol (4.05 g) and Carbopol polymer (250 mg) were added under stirring to form a uniform viscous gel.

Example 18

Granule formation: Guggulsteryl sulfate (250 g), Aerosil 200 (2.8 g), and cross carmellose sodium (15.2 g) were co-sifted together through 20 # sieve and were then granulated using a solution of polyvinylpyrrolidone (PVP K30) (17.1 g) in purified water (28.51 g). The resulting guggulsteryl sulfate granules were then co-sifted together with silicified microcrystalline cellulose (SMCC HD90) (20.04 g), cross carmellose sodium (6.4 g), and hydrophilic fumed silica (Aerosil 200) (2.0 g) through a 40 # sieve. Separately, thymoquinone (50 g) and Aerosil 200 (2.0 g) were co-sifted together through a 40 # sieve.

The thymoquinone mixture and the guggulsteryl sulfate granules mixture were then mixed together. Stearic acid (1.05 g) was sifted through a 40 # sieve and added to the thymoquinone-guggulsteryl sulfate granules mixture, the blend was lubricated for 5 minutes, and was then compressed into tablets.

Seal Coating: Hydroxypropyl methylcellulose (Hypromellose E5) (20.0 g) was dispersed in isopropyl alcohol (257 g), then dichloromethane (168 g) was added and stirred for 30 minutes. Triethyl citrate (2.0 g) was added to the mixture under stirring.

Separately, micronized talc (5.0 g) was dispersed into an isopropyl alcohol (85 g)-dichloromethane (60 g) mixture and homogenized for 15 minutes. The talc mixture was then added to the Hypromellose E5-Triethyl citrate mixture, and the entire content was stirred for 30 minutes. With this mixture, the seal coating of the tablets was performed in auto coater at inlet temp. 35°–40° C. and bed temp 28°–30° C., for weight gain up to 5%. The tablets were dried for 30 minutes at 30°–32° C. bed temperature.

Enteric Coating: Acryl-EZE® 94 yellow (30 g) was dispersed in isopropyl alcohol: water (95:5 mixture) and stirred for 30 minutes. Using this mixture, enteric coating of seal coated tablets was performed in auto coater at inlet temp. 35°–40° C. and bed temp 28°–30° C. for weight gain up to 5%. The tablets were dried for 30 minutes at 30-32 C bed temperature.

Example 19

Granule formation: Sodium cholesteryl sulfate (250 g), Aerosil 200 (2.8 g), and cross carmellose sodium (15.2 g) were co-sifted together through 20 # sieve and were then granulated using a solution of polyvinylpyrrolidone (PVP K30) (17.1 g) in purified water (28.51 g). The resulting sodium cholesteryl sulfate granules were then co-sifted together with silicified microcrystalline cellulose (SMCC HD90) (20.04 g), cross carmellose sodium (6.4 g), and Aerosil 200 (2.0 g) through 40 # sieve. Separately, thymoquinone (50 g) and Aerosil 200 (2.0 g) were co-sifted together through 40 # sieve.

The thymoquinone mixture and the sodium cholesteryl sulfate granules mixture were then mixed together. Stearic acid (1.05 g) was sifted through 40 # sieve and added to the thymoquinone-sodium cholesteryl sulfate granules mixture, the blend was lubricated for 5 minutes, and was then compressed into tablets.

Seal Coating: Hydroxypropyl methylcellulose (Hypromellose E5) (20.0 g) was dispersed in isopropyl alcohol (257 g), then dichloromethane (168 g) was added and stirred for 30 minutes. Triethyl citrate (2.0 g) was added to the mixture under stirring.

Separately, micronized talc (5.0 g) was dispersed into isopropyl alcohol (85 g)-dichloromethane (60 g) mixture and homogenized for 15 minutes. The talc mixture was then added to the Hypromellose E5-Triethyl citrate mixture and the entire content was stirred for 30 minutes. With this mixture, the seal coating of the tablets was performed in auto coater at inlet temp. 35°-40° C. and bed temp 28°-30° C. for weight gain up to 5%. The tablets were dried for 30 minutes at 30°-32° C. bed temperature.

Enteric Coating: Acryl-EZE® 94 yellow (30 g) was dispersed in isopropyl alcohol: water (95:5 mixture) and stirred for 30 minutes. Using this mixture, enteric coating of seal coated tablets was performed in auto coater at inlet temp. 35°-40° C. and bed temp 28°-30° C. for weight gain up to 5%. The tablets were dried for 30 minutes at 30-32° C. bed temperature.

Example 20

Granule formation: Z-Guggulsterol (250 g), Aerosil 200 (2.8 g), and cross carmellose sodium (15.2 g) were co-sifted together through 20 # sieve and granulated with polyvinylpyrrolidone (PVP K30) (17.1 g) in purified water (28.51 g). The resulting Z-guggulsterol granules were co-sifted together with silicified microcrystalline cellulose (SMCC HD90) (20.04 g), cross carmellose sodium (6.4 g), and hydrophilic fumed silica (Aerosil 200) (2.0 g) through a 40 # sieve. Separately, thymoquinone (50 g), Aerosil 200 (2.0 g) were co-sifted together through a 40 # sieve.

The thymoquinone mixture and the Z-guggulsterol granules mixture were then mixed together. Stearic acid (1.05 g) was sifted through a 40 # sieve and added to Thymoquinone-Z-guggulsterol granules mixture. The blend was lubricated for 5 minutes and was then compressed into tablets.

Seal Coating: Hydroxypropyl methylcellulose (Hypromellose E5) (20.0 g) was dispersed in isopropyl alcohol (257 g) and dichloromethane (168 g) was added and stirred for 30 minutes. Triethyl citrate (2.0 g) was added to the mixture under stirring.

Separately, micronized talc (5.0 g) was dispersed into isopropyl alcohol (85 g)-dichloromethane (60 g) mixture and homogenized for 15 minutes. The talc mixture was then added to the Hypromellose E5-Triethyl citrate mixture and the entire content was stirred for 30 minutes. With this mixture, the seal coating of the tablets was performed in auto coater at inlet temp. 35°-40° C. and bed temp 28°-30° C. for weight gain up to 5%. The tablets were dried for 30 minutes at 30°-32° C. bed temperature.

Enteric Coating: Acryl-EZE® 94 yellow (30 g) was dispersed in isopropyl alcohol: water (95:5 mixture) and stirred for 30 minutes. Using this mixture, enteric coating of seal coated tablets was performed in auto coater at inlet temp. 35°-40° C. and bed temp 28°-30° C. for weight gain up to 5%. The tablets were dried for 30 minutes at 30-32° C. bed temperature.

Example 21

Granule formation: Hydrogenated soy phosphatidylcholine (HSPC) (25 g) and Neusilin US2 (33 g, Intra-granular) were co-sifted together through 30 # sieve and then mixed for 5 minutes in Rapid mixer granular. Separately, thymoquinone (50 g) and Kolliphor TPGS (10 g) were dispersed in a vessel and melt at 46-50° C. (product temperature) in water bath. The melted mixtures were then mixed with HSPC-Neusilin mixture in Rapid mixer granular and granulate it under slow speed of impeller. The solid dispersion was unloaded and allowed to cool at room temperature and storing at 2-8° C. The solid dispersion was sifted through 30 # sieve.

Poloxamer 188 (5 g) was sifted through 60 # sieve. Separately, Neusilin US2 (17.0 g, Extra-granular), silicified microcrystalline cellulose (SMCC HD90) (71.5 g), cross carmellose sodium (25 g), sodium lauryl sulfate (5.0 g), hydrophilic fumed silica (Aerosil 200) (2.5 g), and citric acid anhydrous (2.0 g) were co-sifted through a 40 # sieve. The resulting mixture was then transferred into a blender along with thymoquinone-HSPC and poloxamer mixture and mixed for 10 minutes. Magnesium stearate (4.0 g) was sifted through a 60 # sieve and added to the thymoquinone-HSPC granules mixture, the blend was lubricated for 5 minutes and was then compressed into tablets.

Seal Coating: Opadry 21O590002 clear (12.5 g) was dispersed in isopropyl alcohol under stirring and dichloromethane was added and stirred for 45 minutes. The dispersion was sifted through 100 # sieve. With this mixture, the seal coating of the tablets was performed in auto coater at inlet temp. 38°–45° C. and bed temp 30°–35° C. for weight gain. The tablets were dried for 30 minutes at 30°–35° C. bed temperature.

Enteric Coating: Opadry enteric 94O520111 yellow (15.7 g) was dispersed in isopropyl alcohol: water (95:5) mixture, stirred for 45 minutes and sifted through 100 # sieve. Using this mixture, enteric coating of seal coated tablets was performed in auto coater at inlet temp. 40°–45° C. and bed temp 30°–35° C. for desired weight gain. The tablets were dried for 45 minutes at 30-35° C. bed temperature.

Example 22

Thymoquinone (TQ) in Combination with Metformin (Met) Demonstrated Hypoglycemic Activity that was Greater than Metformin Alone Induction of Experimental Diabetes in Mice: Male ICR (CD-1) mice (8-9 weeks of age) were fasted for 6 hrs. before streptozotocin (STZ) administration. Fresh STZ solution at 15 mg/mL was prepared by dissolving powder STZ into 1 mM citrate buffer (pH 4.5). Mice received i.p. STZ solution of 150 mg/kg. Fasting blood glucose level was measured from tail vein blood. Mice with blood glucose levels of 250 mg/dL or higher were considered to be diabetic. Blood samples with "HI" (>600 mg/dL) reading were diluted with same amount of normal saline before measuring again.

A total of 20 diabetic mice were randomized based on the blood glucose levels into two study groups, group A: Metformin (Met)-treated, and group B: Thymoquinone/Metformin (TQ/Met)-treated groups.

There were 10 animals in each group. Mice in group A received oral administration of Met at a dose of 200 mg/kg every day. Mice in group B received oral administration of Met+TQ (200 mg/kg+50 mg/kg) every day using a 20-Ga stainless feeding needle. Fasting blood glucose level was measured weekly. Over 3-week period, treatment with TQ/Met resulted in a 41.3% decrease in blood glucose level. A 32.5% decrease in blood glucose level was achieved with treatment of Met during same period. In addition, Met/TQ demonstrated more potent hypoglycemic activity than Met alone (p=0.019, ANOVA).

| Group (n = 10) | Blood Glucose Level (mg/dL) | | | |
|---|---|---|---|---|
| | Pre-Treat | 1-Week Treat | 2-Week Treat | 3-Week Treat |
| A: Met 200 mg/kg | 443 ± 102 | 433 ± 115 | 290 ± 84 | 299 ± 96 |
| B: Met/TQ 200/50 mg/kg | 445 ± 94 | 347 ± 95 | 247 ± 68 | 261 ± 70 |

Data represent Mean ± SD, n = 10

Water intake was also estimated by weighing each water bottle before and after a period of 24 hrs. The volume of water consumed was estimated from the weight of water consumed. The volume of water consumed by each cage was normalized with body weight and presented as mL/30 g BW over 24 hrs.

A significant reduction in water from TQ/Met group relative to Met alone was observed, as shown in FIG. 1.

Example 23

Figure 2:
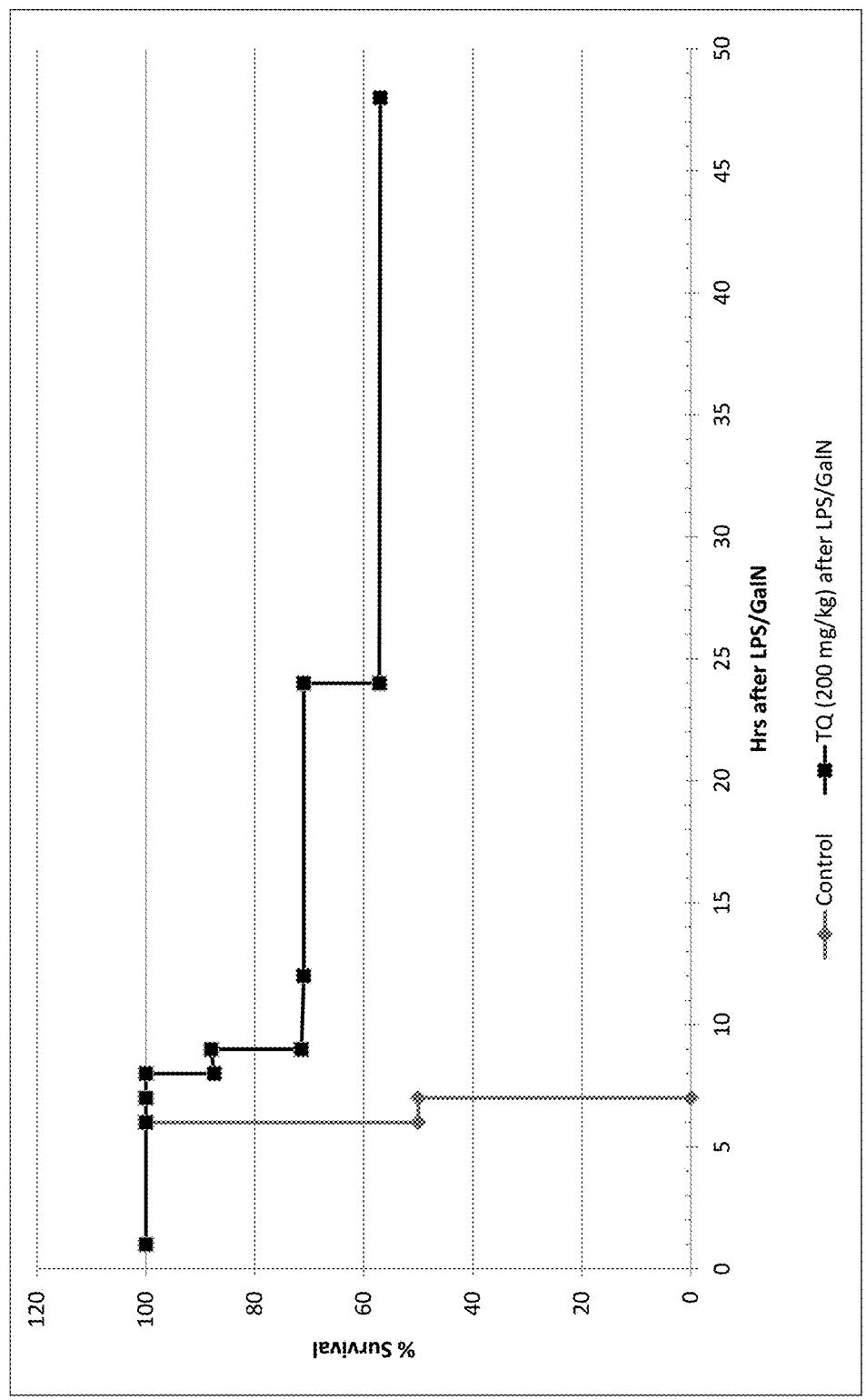
FIG. 2 shows a graph comparing survival rates of mice injected intraperitoneally with D-galactosamine (GalN, Carbosynth) (800 mg/kg) and lipopolysaccharide (LPS from $E$ $coli$ 0127:B8, Sigma-Aldrich) (10 µg/kg) dissolved in normal saline, followed by either purified water (20 mL/kg) for the control group or TQ at a dose of 200 mg/kg, as described in Example 23.

Thymoquinone (TQ) in Lipopolysaccaride/D-Galactosamine (LPS/GalN) Induced Acute Liver Failure in Male C57BL6 Mice A total of 13 male C57BL6 mice (5-6 weeks of age) were injected intraperitoneally with D-galactosamine (GalN, Carbosynth) (800 mg/kg) and lipopolysaccharide (LPS from E coli 0127:B8, Sigma-Aldrich) (10 µg/kg) dissolved in normal saline. 30 min after LPS/GalN injection, 6 mice in the control group received purified water (20 mL/kg) and 7 mice received a TQ at a dose of 200 mg/kg, via oral gavage. Survival was monitored for 48 hrs. All mice in the control group died in over 7 hrs. period following the injection of LPS/GalN, while 4 out of 7 mice treated with TQ survived up to 48 hrs. (see FIG. 2).

Example 24

Figure 3:
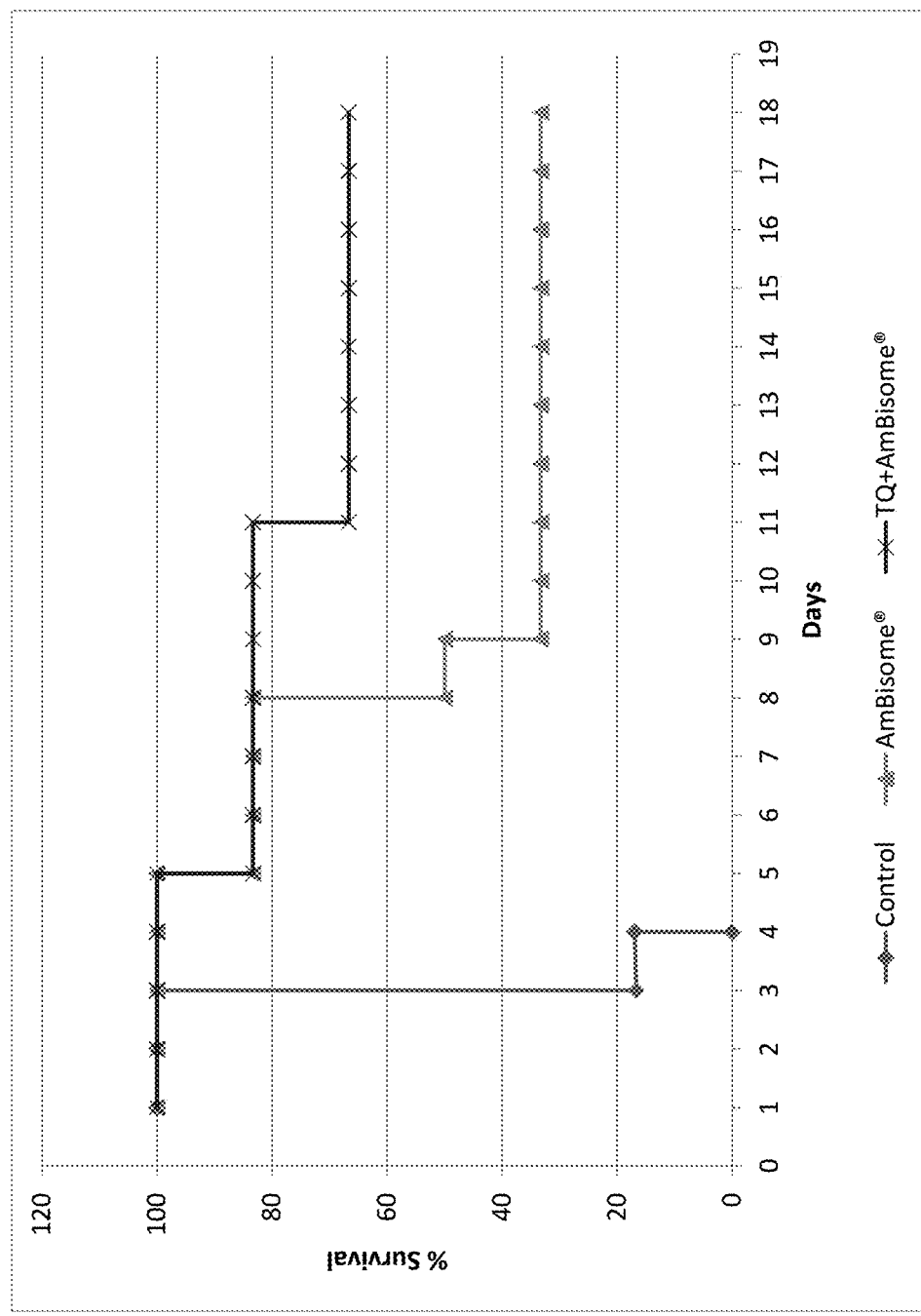
FIG. 3 shows a graph comparing in vivo anti-fungal efficacy of AmBisome® monotherapy to TQ in combination with AmBisome® as evaluated in $A.$ $fumigatus$ infected male ICR (CD-1) mice, as described in Example 24.

Thymoquinone (TQ) in combination with Ambisome® demonstrated anti-fungal Activity that was Greater than Ambisome® Alone The in vivo anti-fungal efficacy of TQ in combination with AmBisome® was evaluated in A. fumigatus infected male ICR (CD-1) mice. Each mouse was i.v. inoculated with $2 \times 10^7$ fungal spores. Three hrs after the spores inoculation, three groups of infected mice were administered with either 5% dextrose (i.v. for 4 days) as non-treatment control, AmBisome® (4 mg/kg, i.v. for 4 days) as monotherapy group or TQ (20 mg/kg, gavage for 4 days) with AmBisome® (4 mg/kg, i.v. for 4 days) as combination therapy group. In control group, 5 out of 6 mice administered with 5% dextrose were found dead on day 3, 1 was found dead on day 4. The median survival was 3 days. Treatment with AmBisome® or TQ+AmBisome® showed significant increase in the survival days. The median survival of mice treated with AmBisome® was 8 days. The median survival of those treated with TQ+AmBisome® was more than 18 days, indicating a significant survival benefit of combination therapy compared to AmBisome® monotherapy (See FIG. 3).

Example 25

Bioanalysis of Thymoquinone Preparation

A thymoquinone preparation as described in Example 20 was spiked into serum and was quantified with a LC-MS/MS method as a thymoquinone derivative, with ascorbic acid used as the derivative agent. Briefly, 2 mL of a 1 M ascorbic acid solution was combined with 8 mL of the spiked serum and mixed gently. The derivative was extracted from the serum mixture with Starta-X 33 Polymeric Reverse Phase (30 mg/mL) cartridges before analysis. Pioglitazone was used as internal standard. This experiment demonstrates a method for quantifying thymoquinone by converting it into its derivative in biological samples such as serum.

All publications and patents mentioned in the above specification are herein incorporated by reference. Various modifications and variations of the described compositions and methods of the invention will be apparent to those skilled in the art without departing from the scope and spirit of the invention. Although the invention has been described in connection with specific preferred embodiments, it should be understood that the invention should not be unduly limited to such specific embodiments. Indeed, various modifications of the described modes for carrying out the invention which are obvious to those skilled in the relevant arts are intended to be within the scope of the following claims.

What is claimed is:

1. A method of preparing a composition comprising a lubricated mixture of thymoquinone-lipid granules, the method comprising:
   i) mixing thymoquinone and vitamin E TPGS and melting it together;
   ii) preparing lipid granules by sifting lipid and magnesium aluminometasilicate and forming a mixture comprising lipid granules and melted thymoquinone of i) and sifting the resulting mixture, wherein the lipid is selected from the group consisting of phosphatidylcholine, guggulsterol, a guggulsterol derivative, and sodium cholesteryl sulfate;

iii) co-sifting magnesium aluminometasilicate, silicified microcrystalline cellulose, cross carmellose sodium, hydrophilic fumed silica; sodium lauryl sulfate, and anhydrous citric acid;

iv) sifting Poloxamer and blending with thymoquinone-lipid granules of ii) and granules of iii); and v) sifting magnesium stearate and combining with the thymoquinone-lipid granules of iv) and mixing to form a lubricated mixture.

2. The method of claim 1, wherein said lubricated mixture of v) is pressed into tablets or formed into capsules, wherein:
   a) the amount of said thymoquinone in a single tablet or capsule is between 10 mg and 2000 mg;
   b) the amount of said phosphatidylcholine in a single tablet or capsule is between 10 mg and 500 mg; and/or
   c) the amount of said guggulsterol or guggulsterol derivative in a single tablet or capsule is between 10 mg and 1000 mg.

3. The method of claim 2, wherein said tablets or capsules are seal-coated with a seal coating.

4. The method of claim 3, wherein said seal coating comprises one or more polymers selected from hydroxymethyl propyl cellulose, methyl hydroxyethylcellulose, ethyl cellulose, hydroxypropylcellulose, hydroxypropyl methylcellulose, povidone, sodium carboxy methylcellulose, acrylate polymer, and polyethylene glycol.

5. The method in claim 4, wherein said seal-coated tablets or capsules are enteric-coated with an enteric coating comprising polymers.

6. The method of claim 5, wherein said enteric coating comprises one or more polymers selected from hydroxypropyl methyl cellulose phthalate, cellulose acetate phthalate, acrylate polymers, and polyvinyl acetate phthalate.

7. The method of claim 1, wherein said phosphatidylcholine comprises one or more of soy phosphatidylcholine, hydrogenated soyphosphatidylcholine, dimyristoylphosphatidylcholine, di stearoylphosphatidylcholine, dipalmitoylphosphatidylcholine, dioleoylphosphatidycholine, and egg phosphatidylcholine.

8. The method of claim 1, wherein said guggulsterol derivative comprises one or more of guggulsteryl sulfate, guggulsteryl phosphate, guggulsteryl phosphocholine, guggulsteryl phosphoglycerol, fatty acid esters of guggulsterol, and a polyethylene glycol (PEG) derivative of guggulsterol.

9. The method of claim 8, wherein the molecular weight of PEG in said PEG derivative of guggulsterol is between 500 and 2000.

10. The method of claim 8, wherein said fatty acid esters of guggulsterol comprise one or more of guggulsteryl acetate, guggulsteryl propionate, guggulsteryl butyrate, guggulsteryl valerate, guggulsteryl hexanoate, guggulsteryl caprylate, guggulsteryl caprates, guggulsteryl laurate, guggulsteryl myrstate, guggulsteryl palmitate, guggulsteryl stearate, guggulsteryl oleate, guggulsteryl linoleate, guggulsteryl linolenate, guggulsteryl eicosapentenoate, guggulsteryl arachidonate, guggulsteryl hemi succinate, and guggulsteryl succinate.

11. A composition comprising a lubricated mixture of thymoquinone-lipid granules prepared by a method comprising:
   i) mixing thymoquinone and vitamin E TPGS and melting it together;

ii) preparing lipid granules by sifting lipid and magnesium aluminometasilicate and forming a mixture comprising lipid granules and melted thymoquinone of i) and sifting the resulting mixture, wherein the lipid is selected from the group consisting of phosphatidylcholine, guggulsterol, a guggulsterol derivative, and sodium cholesteryl sulfate;

iii) co-sifting magnesium aluminometasilicate, silicified microcrystalline cellulose, cross carmellose sodium, hydrophilic fumed silica; sodium lauryl sulfate, and anhydrous citric acid;

iv) sifting Poloxamer and blending with thymoquinone-lipid granules of ii) and granules of iii); and v) sifting magnesium stearate and combining with the thymoquinone-lipid granules of iv) and mixing to form a lubricated mixture.

12. The composition of claim 11, wherein the composition is a tablet or capsule, wherein
   a) the amount of said thymoquinone in a single tablet or capsule is between 10 mg and 2000 mg;
   b) the amount of said phosphatidylcholine in a single tablet or capsule is between 10 mg and 500 mg; and/or
   c) the amount of said guggulsterol or guggulsterol derivative in a single tablet or capsule is between 10 mg and 1000 mg.

13. A method of administering thymoquinone to a subject, comprising:
   i) providing the composition comprising a lubricated mixture of thymoquinone-lipid granules of claim 11; and
   ii) administering the composition to a subject.

14. The composition of claim 12, wherein said tablets or capsules are seal-coated with a seal coating.

15. The composition of claim 14, wherein said seal coating comprises one or more polymers selected from hydroxymethyl propyl cellulose, methyl hydroxyethylcellulose, ethyl cellulose, hydroxypropylcellulose, hydroxypropyl methylcellulose, povidone, sodium carboxy methylcellulose, acrylate polymer, and polyethylene glycol.

16. The composition of claim 14, wherein said seal-coated tablets or capsules are enteric-coated with an enteric coating comprising polymers.

17. The composition of claim 15, wherein said enteric coating comprises one or more polymers selected from hydroxypropyl methyl cellulose phthalate, cellulose acetate phthalate, acrylate polymers, and polyvinyl acetate phthalate.

18. The composition of claim 11, wherein said phosphatidylcholine comprises one or more of soy phosphatidylcholine, hydrogenated soyphosphatidylcholine, dimyristoylphosphatidylcholine, distearoylphosphatidylcholine, dipalmitoylphosphatidylcholine, dioleoylphosphatidycholine, and egg phosphatidylcholine.

19. The composition of claim 11, wherein said guggulsterol derivative comprises one or more of guggulsteryl sulfate, guggulsteryl phosphate, guggulsteryl phosphocholine, guggulsteryl phosphoglycerol, fatty acid esters of guggulsterol, and a polyethylene glycol (PEG) derivative of guggulsterol.

20. The composition of claim 19, wherein the molecular weight of PEG in said PEG derivative of guggulsterol is between 500 and 2000.

21. The composition of claim 19, wherein said fatty acid esters of guggulsterol comprise one or more of guggulsteryl acetate, guggulsteryl propionate, guggulsteryl butyrate, guggulsteryl valerate, guggulsteryl hexanoate, guggulsteryl caprylate, guggulsteryl caprates, guggulsteryl laurate, guggulsteryl myrstate, guggulsteryl palmitate, guggulsteryl stearate, guggulsteryl oleate, guggulsteryl linoleate, guggulsteryl linolenate, guggulsteryl eicosapentenoate, guggulsteryl arachidonate, guggulsteryl hemi succinate, and guggulsteryl succinate.

\* \* \* \* \*